United States Patent [19]

Pelerin

[11] Patent Number: 4,607,120

[45] Date of Patent: Aug. 19, 1986

[54] PROCESS FOR THE PRODUCTION OF SUBSTITUTED BENZOIC ACID ESTERS

[75] Inventor: Gérard Pelerin, Cabris, France

[73] Assignee: Societe Anonyme Roure Bertrand Dupont, Argenteuil, France

[21] Appl. No.: 635,228

[22] Filed: Jul. 27, 1984

[30] Foreign Application Priority Data

Aug. 4, 1983 [CH] Switzerland .................. 4231/83

[51] Int. Cl.⁴ ............................................ C07C 69/88
[52] U.S. Cl. .................................................. 560/070
[58] Field of Search ......................................... 560/70

[56] References Cited

U.S. PATENT DOCUMENTS 4,426,332  1/1984  Thoemel ............................ 560/70

Primary Examiner—Paul J. Killos
Attorney, Agent, or Firm—Sidney Wallenstein; Harry V. Strampel

[57] ABSTRACT

A process for the manufacture of esters of formula

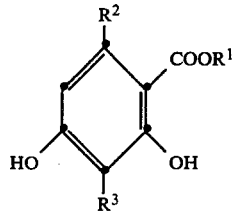

I in which $R^1$ signifies methyl or ethyl and $R^2$ and $R^3$, independently from one another, signify hydrogen or $C_{1-4}$-alkyl, is described. The process comprises treating a diketo ester of the formula

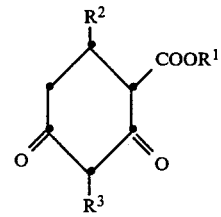

II in which $R^1$ to $R^3$ have the above significances, with the combination of $CuX_2$ and $MeX_n$   III in which Me signifies an alkali metal or alkaline earth metal ion, X signifies halogen and n corresponds to the valency of the metal ion.

Compounds I are known odorants.

The reaction involved is thus an aromatization of the starting material.

13 Claims, No Drawings

PROCESS FOR THE PRODUCTION OF SUBSTITUTED BENZOIC ACID ESTERS

FIELD OF THE INVENTION

The invention relates to the fields of perfumery and organic chemical synthesis.

BACKGROUND OF THE INVENTION

The present invention relates to a process for the preparation of substituted benzoic acid esters. The substituted benzoic acid so prepared are useful as odoriferous agents.

THE PRESENT INVENTION

The invention concerns a process for the production of esters of the general formula

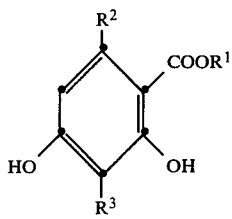

in which $R^1$ signifies methyl or ethyl and
$R^2$ and $R^3$, independently from one another, signify hydrogen or $C_{1-4}$ alkyl,
many of which esters are known.

The process is characterized in treating a diketo ester of the formula

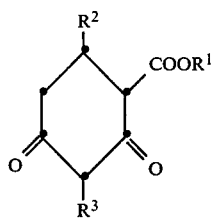

in which $R^1$ to $R^3$ have the above significances, with the combination of $$CuX_2 \text{ and } MeX_n \quad\quad III$$

in which Me signifies an alkali metal or alkaline earth metal ion, X signifies halogen and n corresponds to the valency of the metal ion.

Of most interest are the esters I in which
$R^1$ signifies methyl or ethyl and $R^2$ and $R^3$ signify methyl or $R^2$ signifies methyl and $R^3$ signifies hydrogen.

Especially preferred is the compound with $R^1$, $R^2$ and $R^3$ as methyl.

The compounds I are known odorants, as described in e.g. U.S. Pat. Nos. 3,634,491 and 3,944,596.

DESCRIPTION OF THE PREFERRED EMBODIMENTS

The reaction according to the invention is suitably carried out in a solvent, preferably a polar solvent. Especially preferred polar solvents are the polar aprotic solvents, e.g. dimethylformamide, acetonitrile, or ethers, especially diisopropyl ether. However, non-polar aprotic solvents, such as chlorinated hydrocarbons, e.g. dichloroethane, or polar protic solvents, such as alcohols, are also suitable.

In the definition X signifies halogen, whereby all halogens, i.e. F, Cl, Br and I are suitable. Me signifies in the definition an alkali metal or alkaline earth metal ion, whereby all such metals, in particular Li, Na, K and Ca, Sr, Ba are possible. The ratio of Cu to Me in the compounds III is suitably 1–5:1, preferably 1–2:1. The ratio of compound II to compounds III (relative to Cu) is suitably 0.1–0.5:1, preferably 0.4–0.5:1.

The process of the invention is suitably effected in a temperature range from approximately 50° C. to approximately 120° C.; the preferred temperature range is that from approximately 55° C. to approximately 80° C.

The production of the esters I can generally be carried out in the following manner:

The keto ester II, the copper halide and the helide $MeX_n$ are suspended in the solvent. Then the suspension is heated to approximately 50° C.–120° C. and the course of the reaction is followed chromatographically, e.g. by thin layer chromatography. After completion of the reaction the reaction mixture is cooled. The solution is then treated with an excess of a mineral acid, preferably, e.g. a 10% aqueous solution of hydrogen chloride. When a solvent which is completely miscible with water is chosen, such as dimethylformamide or acetonitrile, the reaction mixture is subsequently taken up into a solvent which is immiscible with water. Examples of such latter solvents are 1,2-dichloroethane and diisopropyl ether. Thereafter the organic phase is separated from the aqueous phase, and the latter is extracted. The organic phases are washed with water to neutrality. The solvent is distilled off, and the crude reaction product I is purified, for example by chromatography, crystallization or sublimation.

The reaction of diketo esters of formula II to esters of formula I in a two-step reaction using $CuBr_2$ in the first step, has been described by R. S. Marmor, J. Org. Chem. 37, (1972), 2901 seq. The yield of I starting from II was, however, only 41–43%.

Furthermore, Pfau et al., Helv. Chim. Acta 16, (1933), 282 seq. describe the reaction of II→I using $FeCl_3$. The yield of this transformation is described to be poor. It is thus most surprising that the use of the couple $CuX_2 + MeX_n$ in the present essentially one-step process leads to a substantial increase in the yield of I starting from II, i.e. in most cases above 70%.

EXAMPLE

To a reaction vessel fitted with stirrer, thermometer and reflux cooler are added 99 g (0,5 mole) of methyl 3,6-dimethylcyclohexane-2,4-dione carboxylate 500 ml of acetonitrile, 170.5 g of cupric chloride dihydrate (1 mole) and 50.8 g (0,25 mole) magnesium chloride hexahydrate. The reaction mixture is heated for 8 hours under reflux, after which time the complete disappearence of the dione is established. The mixture is taken up in 250 ml of diisopropyl ether and washed with 250 ml of 10% hydrochloric acid. The decanted aqueous phase is extracted twice with 250 ml of diisopropyl ether. Then the combined organic phases are washed twice with two 250 ml amounts of 10% hydrochloric acid, followed by three 250 ml amounts of water. The solvents are distilled off. Then the obtained crude dihydroxy derivative is recrystallized from 250 ml of toluene and twice from 50% methanol, whereby the recrystallizations are effected under a nitrogen atmosphere. 74,5 g (yield 76%) of ochre-yellow crystals of methyl β-orcine carboxylate are obtained; Mp.: 143°–144° C.

By means of infrared and NMR spectroscopy the product is identified as the compound of the formula

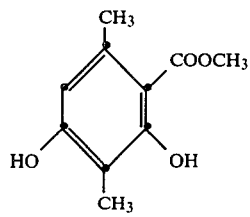

In an analogous manner the monomethyl derivative of the above formula I is obtained from methyl 6-methylcyclohexane-2,4-dione carboxylate and the corresponding ethyl orcine carboxylate from ethyl 6-methylcyclohexane-2,4-dione carboxylate.

Variation of parameters:

| solvent | combination III | yield* |
|---|---|---|
| DMF | $CuCl_2 \cdot 2H_2O$ — $CaCl_2$ | 55% |
| $CH_3CN$ | $CuCl_2 \cdot 2H_2O$ — $BaCl_2 \cdot 2H_2O$ | 86% |
| $CH_3CN$ | $CuCl_2 \cdot 2H_2O$ — Na I $\cdot 2H_2O$ | 81% |
| $CH_3CN$ | $CuCl_2 \cdot 2H_2O$ — NaCl | 76% |
| $CH_3CN$ | $CuBr_2$ — $CaCl_2$ | 58% |
| $(CH_3)_2CHOCH(CH_3)_2$ | $CuBr_2$ — LiBr | 76% |

*production of methyl β-orcinecarboxylate.

I claim:

1. A process for the production of esters of the general formula

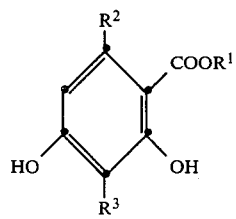

in which $R^1$ signifies methyl or ethyl and $R^2$ and $R^3$, independently from one another, signify hydrogen or $C_{1-4}$-alkyl, characterized in treating a diketo ester of the general formula

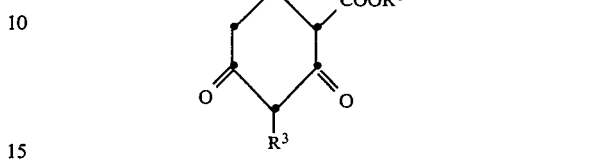

in which $R^1$ to $R^3$ have the above significances, with the combination of

$CuX_2$ and $MeX_n$       III in which Me signifies an alkali metal or alkaline earth metal ion, X signifies halogen and n corresponds to the valency of the metal ion.

2. A process according to claim 1, characterized in that $R^1$=methyl or ethyl and $R^2$=$R^3$=methyl or $R^1$=methyl or ethyl, $R^2$=methyl and $R^3$=hydrogen.

3. A process according to claim 1, characterized in that the reaction is carried out in a polar, especially polar aprotic, solvent.

4. A process according to claim 1, characterized in that the reaction in carried out in an ether.

5. A process according to claim 4, characterized in that the reaction is carried out in diisopropyl ether.

6. A process according to claim 1, characterized in that X signifies chlorine.

7. A process according to claim 1, characterized in that Me signifies calcium.

8. A process according to claim 1, characterized in that the ratio of Cu to Me is 1–5:1.

9. A process according to claim 8, characterized in that the ratio of Cu to Me is 1–2:1.

10. A process according to claim 9, characterized in that the ratio of II:III (relative to Cu) is 0.1–0.5:1.

11. A process according to claim 10, characterized in that the ratio of II:III is 0.4–0.5:1.

12. A process according to claim 11, characterized in that the reaction is carried out in a temperature range of approximately 50° C. to approximately 120° C.

13. A process according to claim 12, characterized in that the reaction is carried out in a temperature range of approximately 55° C. to approximately 80° C.

* * * * *